(12) United States Patent
Briffaud et al.

(10) Patent No.: US 10,683,258 B2
(45) Date of Patent: Jun. 16, 2020

(54) COMPOSITION MADE OF AMINO ACID OR ESTER WITH POLYMER QUALITY AND METHODS FOR OBTAINING SAME

(71) Applicant: ARKEMA FRANCE, Colombes (FR)

(72) Inventors: Thierry Briffaud, Bernay (FR);
Jean-Luc Couturier, Lyons (FR);
Jean-Luc Dubois, Millery (FR);
Jean-François Devaux, Soucieu en Jarrest (FR)

(73) Assignee: ARKEMA FRANCE, Colombes (FR)

(*) Notice: Subject to any disclaimer, the term of this patent is extended or adjusted under 35 U.S.C. 154(b) by 111 days.

(21) Appl. No.: 15/764,596

(22) PCT Filed: Sep. 28, 2016

(86) PCT No.: PCT/FR2016/052466
§ 371 (c)(1),
(2) Date: Mar. 29, 2018

(87) PCT Pub. No.: WO2017/055745
PCT Pub. Date: Apr. 6, 2017

(65) Prior Publication Data
US 2018/0282259 A1    Oct. 4, 2018

(30) Foreign Application Priority Data
Sep. 30, 2015 (FR) ..................... 15 59260

(51) Int. Cl.
| | | |
|---|---|---|
| *C07C 227/14* | (2006.01) | |
| *C07C 227/04* | (2006.01) | |
| *C08G 69/08* | (2006.01) | |
| *C07C 227/40* | (2006.01) | |
| *C08G 69/04* | (2006.01) | |

(52) U.S. Cl.
CPC .......... *C07C 227/04* (2013.01); *C07C 227/40* (2013.01); *C08G 69/04* (2013.01); *C08G 69/08* (2013.01)

(58) Field of Classification Search
CPC .................................................. C07C 227/04
See application file for complete search history.

(56) References Cited

U.S. PATENT DOCUMENTS

| | | |
|---|---|---|
| 2010/0168453 A1 | 7/2010 | Dubois et al. |
| 2014/0178948 A1* | 6/2014 | Schaffer .............. C12P 13/001 |
| | | 435/128 |

FOREIGN PATENT DOCUMENTS

| | | |
|---|---|---|
| WO | 2008/104722 A2 | 9/2008 |
| WO | 2010/089512 A1 | 8/2010 |
| WO | 2013/017782 A1 | 2/2013 |
| WO | 2013/017786 A1 | 2/2013 |
| WO | 2013/030481 A1 | 3/2013 |
| WO | 2014/106723 A1 | 7/2014 |
| WO | 2014/106724 A1 | 7/2014 |
| WO | 2014/106766 A1 | 7/2014 |
| WO | 2014/122410 A2 | 8/2014 |
| WO | 2014/122412 A1 | 8/2014 |
| WO | 2014/147337 A1 | 9/2014 |
| WO | 2015/071604 A1 | 5/2015 |

OTHER PUBLICATIONS

International Search Report (PCT/ISA/210) dated Jan. 16, 2017, by the French Patent Office as the International Searching Authority for International Application No. PCT/FR2016/052466.
Written Opinion (PCT/ISA/237) dated Jan. 16, 2017, by the French Patent Office as the International Searching Authority for International Application No. PCT/FR2016/052466.

* cited by examiner

*Primary Examiner* — Gregory Listvoyb
(74) *Attorney, Agent, or Firm* — Thomas F. Roland

(57) ABSTRACT

The present invention relates to a composition which comprises at least one α,ω-amino-alkanoic acid or ester and at least one alkanoic ester or acid, characterised in that: the α,ω-amino-alkanoic acid or ester has formula $H_2N-(CH_2)_n-COOR$, wherein n=9 to 13 and R is an alkyl group or a hydrogen; the alkanoic ester or acid has formula $R_1-COOR_2$, wherein $R_1$ is a straight or branched alkyl group with formula $C_mH_{2m+1}$ or $C_mH_{2m-3}$, wherein m=6 to 20 and $R_2$ is an alkyl group or a hydrogen; the molar ratio between the alkanoic acid(s) or ester(s) and the α,ω-amino-alkanoic acid(s) or ester(s) is in the range from 0.001 to 0.4%. The present invention also relates to novel methods for obtaining such a composition.

13 Claims, No Drawings

COMPOSITION MADE OF AMINO ACID OR ESTER WITH POLYMER QUALITY AND METHODS FOR OBTAINING SAME

FIELD OF THE INVENTION

The subject of the invention is a composition based on long-chain α,ω-aminoalkanoic acid or ester and on alkanoic acid or ester, and the processes for obtaining this composition. This composition according to the invention can be used in particular as starting material for the production of polyamides or copolyamides.

TECHNICAL BACKGROUND

The polyamide industry uses an entire range of monomers formed from diamines and from diacids, from lactams, and especially from α,ω-amino acids. These monomers are defined by the length of the methylene chain $(-CH_2)_n$ separating two amide functions —CO—NH—.

For the purposes of the invention, the term "α,ω-aminoalkanoic acids or esters", hereinafter simply "amino acids or amino esters", is in fact intended to mean any long-chain α,ω-amino acid, that is to say the chain of which comprises at least 8 carbon atoms.

Indeed, the polyamides targeted by the present invention are technical polyamides, that is to say high-performance, or even very-high-performance, polyamides produced from monomers comprising at least 8 carbon atoms, preferably at least 10 carbon atoms; as opposed to the "commodity" polyamides, such as nylon 6, of which the amounts (volumes) sold are much greater and the costs much lower than those of the technical polyamides.

Polymerization from long-chain α,ω-aminoalkanoic acid or ester monomers, in order to achieve high degrees of polymerization (greater than 80), requires monomers of high purity.

Among the most promising processes for producing long-chain α,ω-aminoalkanoic acid or ester, mention may be made of processes for hydrogenation of unsaturated acid nitriles or unsaturated nitrile esters, such as those described in patent applications WO 08/104722 and WO 14/122412. These patent applications describe a process for synthesis of amino acid by metathesis, hydrolysis, then hydrogenation.

During tests for producing polyamides from these long-chain α,ω-aminoalkanoic acids or esters, two problems have been revealed. In some cases, it is not possible to obtain polyamides with a high degree of polymerization. In other cases, the melt rheology of the polyamide obtained is unstable at high temperature, about from 200 to 350° C. for example: the melt viscosity tends to increase. This instability can, during the conversion of the granules into molded or extruded pieces (and in particular during an unforeseen machine stop), lead to a blocking of the injection or extrusion screws because of the excessively high viscosity reached. This blocking has several drawbacks: It is necessary to disassemble and clean the machine before starting up again, which leads to a loss of production time, or even a degradation of the material.

There is therefore a real need to find starting materials based on long-chain α,ω-aminoalkanoic acid or ester which make it possible to produce long-chain polyamides with a high degree of polymerization, and which are stable at high temperature, that is to say the melt viscosity of which does not increase.

The applicant has now found a composition based on long-chain α,ω-aminoalkanoic acid or ester, which makes it possible to achieve these two objectives, by combining the α,ω-aminoalkanoic acid or ester with a particular content of alkanoic acid or ester. The latter has in fact been identified by the inventors as a key element of the composition for producing long-chain polyamides with a high degree of polymerization and which are stable at high temperature.

DESCRIPTION OF THE INVENTION

Throughout the text, the pressures are expressed in bar or mbar absolute. A subject of the present invention is therefore a composition comprising at least one α,ω-aminoalkanoic ester or acid and at least one alkanoic acid or ester, characterized in that:

the α,ω-aminoalkanoic ester or acid has the formula $H_2N-(CH_2)_n-COOR$ avec n=9 to 13 and R is an alkyl group or a hydrogen, the alkanoic acid or ester has the formula R1-COOR2 with R1 being a linear or branched alkyl group of formula $C_mH_{2m+1}$ or $C_mH_{2m-1}$ or $C_mH_{2m-3}$ where m=6 to 20 and R2 is an alkyl group or a hydrogen, the molar ratio between alkanoic acid(s) or ester(s) and α,ω-aminoalkanoic ester(s) or acid(s) is in the range of between 0.001% and 0.4% and preferably between 0.01% and 0.2% and more preferentially between 0.02% and 0.1%.

Advantageously, n=10 or 11 and R is a methyl or ethyl or butyl group or a hydrogen.

Preferably, R1 is a linear alkyl group of composition $C_n-1H_{2n-1}$ and R2 is a methyl or ethyl group or a hydrogen.

Advantageously, the composition according to the invention also comprises at least one acid nitrile or one nitrile ester of formula $NC-(CH_2)_{(n-1)}-COOR$, in which the molar ratio of nitrile relative to the α,ω-aminoalkanoic ester or acid is in the range of from 0.0001% to 0.5%, preferably in the range of from 0.0001% to 0.1%, preferably in the range of from 0.0001% to 0.05%.

Advantageously, the composition according to the invention also comprises at least one secondary amine of formula $ROOC-(CH_2)_n-NH-(CH_2)_n-COOR$, in which the molar ratio relative to the α,ω-aminoalkanoic ester or acid is in the range of from 0.0001% to 1%, preferably from 0.0001% to 0.5%.

Advantageously, the composition according to the invention also comprises at least one $ROOC-(CH_2)_n-NH-CO-(CH_2)_n-NH_2$ dimer, the molar ratio of dimer relative to the α,ω-aminoalkanoic ester or acid being in the range of from 0.0001% to 5% and preferably in the range of from 0.0001% to 1%.

Advantageously, the composition according to the invention also comprises at least one compound chosen from: compounds that are inert with respect to the polymerization, alcohols, water, and mixtures thereof.

The compounds that are inert with respect to the polymerization are advantageously chosen from: aromatic hydrocarbons, such as benzene, toluene, xylene or ethylbenzene; aliphatic hydrocarbons, such as cyclohexane, methylcyclohexane, pentane or heptane; or an aliphatic fraction, or an ether such as tetrahydrofuran, diethyl ether, diisopropyl ether or methyl tert-butyl ether; and mixtures thereof.

The alcohols are advantageously chosen from methanol, ethanol, butanol, and mixtures thereof.

Preferably, the optional content of inert compounds, of alcohol and/or of water of the present composition is less than 90%, preferably less than 50%, preferably less than 10%, and more preferentially less than 2%, by weight relative to the total weight of the composition.

Preferably, the optional content of α,ω-aminoalkanoic ester or acid is greater than 10%, preferably greater than 50%, preferably greater than 90% and more preferably greater than 98%, by weight relative to the total weight of the composition.

Another subject of the present invention is a polymer, in particular a polyamide, obtained by polymerization starting from the composition according to the invention.

The present invention also describes two novel possible processes (hereinafter process A and process B) for preparing such a composition of long-chain α,ω-aminoalkanoic ester and of alkanoic acid or ester in which the molar ratio between the alkanoic acid or ester and the long-chain α,ω-aminoalkanoic ester is in the range of from 0.001% to 0.4%, starting from unsaturated nitrile ester. The entire technical challenge of these processes is to succeed in limiting the alkanoic acid/ester content in the composition to a content of less than 0.4%, and to obtain a good chemical yield, greater than 70%, preferably greater than 80% and preferably greater than 90%.

PROCESSES FOR PREPARING THE COMPOSITION

Process A

According to a first embodiment, the composition according to the invention is produced by a hydrogenation reaction starting from an unsaturated aliphatic acid nitrile or from an unsaturated aliphatic nitrile ester such that:
- the unsaturated acid nitrile or nitrile ester contains less than 0.3% of alkanoic acid or ester, preferably from 0.001% to 0.3%, and preferably less than 0.1%, preferably from 0.001% to 0.1%, of alkanoic acid/ester;
- the hydrogenation is carried out in the presence of a heterogeneous catalyst which comprises at least Co and/or Ru;
- the hydrogenation is carried out in the presence of a base.

Preferentially, the process also comprises a step of separating heavy compounds on an apparatus with a short residence time.

Process B

According to a second embodiment, the composition according to the invention can also be produced by a sequence of two hydrogenation steps starting from an unsaturated aliphatic acid nitrile or from an unsaturated aliphatic nitrile ester such that:
- the unsaturated acid nitrile or nitrile ester contains as impurity less than 0.3% of alkanoic acid or ester, preferably from 0.001% to 0.3%, and preferably less than 0.1%, preferably from 0.001% to 0.1%, of alkanoic acid/ester;
- the role of the first hydrogenation step is to partially or totally convert the unsaturated aliphatic acid nitrile or the unsaturated aliphatic nitrile ester into a saturated aliphatic nitrile or ester and it is carried out in the presence of a heterogeneous catalyst comprising at least palladium and/or rhodium and/or platinum;
- the object of the second step is to form the saturated amino acid or ester and it is carried out on a heterogeneous catalyst which comprises at least Ni and/or Co and/or Ru.

Preferentially, the process also comprises a step of separating heavy compounds on an apparatus with a short residence time.

In the two process cases, the unsaturated aliphatic nitrile ester/acid nitrile has the formula:

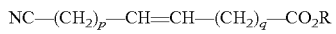

With p>=0 and q>=0 and p+q+3=n defined previously
R defined as previously.

The double bond is without distinction cis or trans. It is preferably a cis and trans mixture.

It can be produced by metathesis, in particular according to the processes described in: WO 2008/104722, WO 10/089512, WO 13/017782, WO 13/017786, WO 13/030481, WO 14/106766, WO 14/106723, WO 14/106724, WO 14/147337. Preferably, a crude mixture resulting from the metathesis reaction is subjected to purification steps. These purifications are for example steps to remove or inactivate the metathesis catalyst, distillation steps to remove the solvent and/or reagents or light impurities, and/or heavy impurities. The reagents removed are for example esters or acids or nitriles. The heavy impurities removed may for example be fatty acids or esters, such as methyl oleate, or diesters such as the compound $RO_2C-(CH_2)_q-CH=CH-(CH_2)_q-CO_2R$.

The (mixture thus obtained based on) unsaturated aliphatic nitrile ester or the unsaturated aliphatic acid nitrile used contains less than 0.3% of alkanoic acid or ester and preferably less than 0.1%.

Preferably, the unsaturated aliphatic nitrile ester or the unsaturated aliphatic acid nitrile contains less than 1% and preferably less than 0.1% of diester.

Characteristics Specific to Process A:

The hydrogenation is carried out in the presence of at least one heterogeneous hydrogenation catalyst which contains at least cobalt and/or ruthenium.

The catalyst according to the invention typically contains 0.1% to 10% of ruthenium and preferably 1% to 5%, and/or 1% to 90% of cobalt and preferably 5% to 60%.

The cobalt and/or the ruthenium are preferably in the reduced metal form thereof.

The catalyst introduced into the reactors according to the invention can nevertheless contain ruthenium oxides or cobalt oxides, for example in the form of a passivation layer.

In addition to the cobalt or ruthenium, the catalyst can contain other metals, such as iron, nickel, chromium, manganese, rhodium, osmium, iridium, platinum or palladium. The catalyst can also be doped with alkali metals such as sodium, potassium, rubidium or cesium, or alkaline-earth metals such as magnesium, calcium, strontium or barium.

The catalyst may be in the finely divided state, for example in the form of a Raney catalyst. It may also be in the form of granules, or alternatively may be deposited on a support. Examples of appropriate supports are pumice stone, titanium dioxide, carbon, charcoal, silicon carbide (preferably of beta SiC form), alumina, silica, a mixture of silica and alumina, and steatite.

The catalyst in granular form or deposited on a support may be in any form, such as: sphere, grain, hollow cylinder, three-lobed and four-lobed, and also in the form of cylinders, which have been extruded or compressed, optionally using a pelleting agent.

The preparation of the finely divided catalysts of Raney type is widely known in the art.

The catalysts may be prepared via the methods known for charging metals onto a support. For example, a catalyst can be prepared by bringing the support into contact with an aqueous or alcoholic solution of ruthenium trichloride, ruthenium nitrosylnitrate, or any water-soluble or alcohol-soluble ruthenium salt, of cobalt carbonate, of cobalt nitrate or any water-soluble or alcohol-soluble cobalt salt, then by evaporating off the water or the alcohol and by activating the catalyst using means of heating and of reduction in a gas stream containing hydrogen. The cobalt-containing catalysts will be calcined typically at temperatures of from 300 to 500° C. and reduced at temperatures of from 300 to 500° C. The ruthenium catalysts will be calcined typically at temperatures of from 200 to 400° C. and reduced at temperatures of from 100 to 400° C.

The other metals, such as iron, nickel, chromium, magnesium, rhodium, osmium, iridium, platinum or palladium, and also the alkali or alkaline-earth metals, can be introduced onto the catalyst in the same way as the ruthenium or cobalt, either prior to bringing the ruthenium salt or cobalt salt solution into contact with the support, or concomitantly, or in a subsequent step.

The catalyst can also be prepared by known precipitation or co-precipitation techniques, followed by steps of calcination and reduction in a gas stream containing hydrogen. The precipitation steps make it possible to obtain a solid containing cobalt mainly in the form of CoO, $Co_3O_4$ and/or CoO(OH), optionally doped with iron, nickel, chromium, manganese, rhodium, osmium, iridium, platinum or palladium, or alkali or alkaline-earth metals or silica or alumina or a mixture of silica and alumina. The solid can undergo calcination at a typical temperature of from 300 to 500° C. and it is reduced in a gas stream containing hydrogen at temperatures of from 300 to 500° C.

The catalysts used can be air-sensitive, or even pyrophoric. They can undergo a passivation step so as to be able to charge the hydrogenation reactors without risk. There are numerous passivation techniques. For example, they can be passivated with depleted air or with air at a temperature close to ambient temperature, or else with sulfur compounds. They can be encapsulated in paraffins or saturated esters which will melt when the reactor starts and be eliminated in the reaction medium. They can also be conditioned and manipulated in the presence of water or of an organic solvent.

Advantageously, the hydrogenation reaction is carried out at a pressure in the range of from 5 to 100 bar, preferably from 20 to 80 bar.

Advantageously, the temperature is in the range of from 50 to 150° C., preferably from 80 to 110° C.

A base is added in order to reduce the selectivity with respect to secondary amine. The base can typically be sodium hydroxide, sodium methoxide, potassium hydroxide, potassium tert-butoxide or ammonia, and mixtures thereof. Ammonia is preferably used. The base/unsaturated nitrile ester molar ratio is typically in the range of from 0.1 to 4 and preferably from 0.3 to 2.5.

According to one embodiment, the hydrogenation is carried out in the absence of solvent.

According to one preferred embodiment, the hydrogenation is carried out in the presence of a solvent. The solvent may be an aromatic hydrocarbon, such as benzene, toluene, xylene or ethylbenzene, or an aliphatic hydrocarbon, such as cyclohexane, pentane, heptane or methylcyclohexane, or an aliphatic fraction, or an alcohol, such as methanol, ethanol, propanol or isopropanol, butanol or an isomer, or an ester such as ethyl acetate or methyl acetate, or an ether such as tetrahydrofuran, diethyl ether, diisopropyl ether, methyl tert-butyl ether or an amide such as dimethylformamide or N-methylpyrrolidone, or a carbonate such as dimethyl carbonate, diethyl carbonate, ethylene carbonate or propylene carbonate; or else a mixture of these solvents.

Preferably, the solvent comprises: toluene, xylene, cyclohexane or methylcyclohexane, or mixtures thereof.

The concentration of unsaturated nitrile ester/acid nitrile in the solvent can range from 1% to 70% and preferably from 10% to 50% by weight.

The amount of hydrogen used is preferably in the range of from 3 to 200 mol per 1 mol of unsaturated nitrile ester/acid nitrile. The hydrogen $H_2$ partial pressure is at least 5 bar and at most 100 bar and preferably at least 15 bar and at most 80 bar.

Type of Reactor:

The unsaturated nitrile ester/acid nitrile optionally mixed with a solvent and/or base forms a liquid phase which is brought into contact with the solid catalyst in any suitable way, and hydrogen gas is brought into contact with the solid catalyst and the liquid phase.

In the case where a finely divided catalyst is used, it may be dispersed in the liquid phase, and maintained in dispersion by stirring. This stirring can be carried out in a reactor equipped with a stirrer, preferably a self-suction turbine, by means of a recirculation equipped with a liquid gas ejector (jet loop, Buss loop). [description http://www.airproducts.com/~/media/downloads/h/hydrogen-support-microsite/hydrogen-support-increasing-productivity-in-slurry-hydrogenation-process.pdf]. In this case, the catalyst particle size is preferably less than 1 mm, typically in the range of from 1 to 100 μm. A continuous oscillatory baffled reactor may also be used.

An easy means for performing the hydrogenation consists in using a bed of pellets or granules of solid catalyst. The liquid phase may be passed over the catalyst, by flow in the same direction or in counter-current to a hydrogen stream. The bed of catalyst may be completely immersed in the solution, or the bed may be used in the form of a trickle bed. In this case, the catalyst particle size will be in the range of from 1 to 10 mm and preferably in the range of 1 to 5 mm. Use may also be made of a catalyst in the form of a structured monolith (for example in the form of a ceramic foam, such as an SiC foam serving as support for the active phase).

The reaction may be performed batchwise via successive charges (in batch form) or continuously.

When a new batch of catalyst is charged to a reactor, the latter may undergo conditioning before being brought into contact with the unsaturated nitrile ester.

This conditioning may consist of steps of inerting, heat treatments and/or the injection of hydrogen in increasing concentration.

The heat generated by the reaction can be discharged by any means known to those skilled in the art: by heat exchangers located inside the reactor or located on a recirculation loop external to the reactor or by circulation of a cooling fluid in the case of a jacketed reactor or of a multitubular reactor or plate reactor; or else by multi-stage injection of cold reagent, such as cold hydrogen.

The amounts of catalyst to be used vary according to the activity of the catalyst and the reaction conditions, in particular the temperature and pressure conditions. In successive-charge operations, the weight ratio of catalyst relative to the weight of unsaturated nitrile ester can range from 0.01 to 1 and preferably from 0.05 to 0.3. The reaction time is in the range of from 1 h to 24 h and preferably in the range of from 3 h to 15 h. In continuous operations, the liquid space velocity of the catalyst, expressed in kg/h of unsaturated nitrile ester divided by kgs of catalyst, can range from 0.01 to 10 $h^{-1}$ and preferably from 0.05 to 2 $h^{-1}$.

It is the choice of the catalyst previously described which makes it possible to limit the production of alkanoic esters/acids relative to the amount of α,ω-aminoalkanoic ester or acid in the hydrogenation step.

By hydrogenating, according to the process described, an unsaturated nitrile ester/acid nitrile containing less than 0.3% of alkanoic acid or ester, a composition is obtained which contains a molar ratio between the alkanoic acids or esters and the α,ω-aminoalkanoic ester or acid in the range of from 0.001% to 0.4%.

Under these conditions, those skilled in the art know how to adjust the hydrogenation reaction conditions (amount of catalyst, pressure, temperature) so as to maximize the conversion of the unsaturated nitrile ester/acid nitrile and to obtain a content of saturated nitrile ester/acid nitrile which forms that is intermediately in the range of from 0.0001 mol % to 0.5 mol % and preferably from 0.0001 mol % to 0.1 mol % relative to the α,ω-aminoalkanoic ester or acid.

Characteristics Specific to Process B:

The first hydrogenation step is carried out on a heterogeneous catalyst which contains at least palladium or rhodium or platinum, or mixtures thereof, preferably at least palladium.

The catalyst according to the invention typically contains from 0.1% to 10% of palladium or rhodium and/or platinum, and preferably from 0.2% to 5%.

The palladium or the rhodium or the platinum is advantageously placed on a support. Examples of appropriate supports are pumice stone, titanium dioxide, carbon, charcoal, silicon carbide (preferably of beta SiC form), alumina, silica, a mixture of silica and alumina, steatite or calcium carbonate.

The catalyst may be in any form, such as: powder, sphere, grain, hollow cylinder, three-lobed and four-lobed, and also in the form of cylinders, which have been extruded or compressed, optionally using a pelleting agent.

Advantageously, the first hydrogenation reaction is carried out at a pressure in the range of from 1 to 90 bar, preferably from 1 to 50 bar, preferably from 2 to 20 bar, preferably from 2 to 10 bar.

Advantageously, the temperature is in the range of from 10 to 100° C., preferably from 20 to 100° C., preferably in the range of from 20 to 50° C., preferably from 30 to 50° C. This step is generally carried out without solvent.

According to another embodiment, the hydrogenation is carried out in the presence of a solvent. The solvent may be an aromatic hydrocarbon, such as benzene, toluene, xylene or ethylbenzene, or an aliphatic hydrocarbon, such as cyclohexane, pentane, heptane or methylcyclohexane, or an aliphatic fraction, or an alcohol, such as methanol, ethanol, propanol or isopropanol, butanol or an isomer, or an ester such as ethyl acetate or methyl acetate, or an ether such as tetrahydrofuran, diethyl ether, diisopropyl ether, methyl tert-butyl ether or an amide such as dimethylformamide or N-methylpyrrolidone, or a carbonate such as dimethyl carbonate, diethyl carbonate, ethylene carbonate or propylene carbonate; and mixtures thereof.

Preferably, the solvent is chosen from toluene, xylene, cyclohexane or methylcyclohexane, or mixtures thereof.

The concentration of unsaturated nitrile ester in the solvent can range from 1% to 70% and preferably from 10% to 50% by weight.

The reaction may be performed batchwise via successive loads or continuously.

The amounts of catalyst to be used vary according to the activity of the catalyst and the reaction conditions, in particular the temperature and pressure conditions.

In successive-charge operations, the weight ratio of catalyst relative to the weight of unsaturated nitrile ester can range from 0.01 to 1 and preferably from 0.05 to 0.3. The reaction time is in the range of from 30 minutes to 24 h and preferably in the range from 1 h to 10 h. In continuous operations, the liquid space velocity of the catalyst, expressed in kg/h of nitrile ester/acid nitrile divided by kg of catalyst, can range from 0.01 to 10 $h^{-1}$, preferably from 0.05 to 6 $h^{-1}$, preferably from 0.05 to 4 $h^{-1}$, preferably from 0.05 to 2 $h^{-1}$, preferably from 0.2 to 2 $h^{-1}$, preferably from 0.5 to 2 $h^{-1}$. The following will be adjusted under these conditions: the amounts of catalysts used, the reaction temperature, pressure and time or the space velocity so as to convert more than 70% of the unsaturated nitrile ester and preferably more than 90% and more preferentially more than 95%. The product formed is predominantly the saturated nitrile ester/acid nitrile of formula $NC-(CH_2)_{(p+q+2)}-CO_2R$, with a degree of conversion in the range of from 70% to 99.5%, preferably in the range of from 80% to 99%, preferably in the range of from 90 to 99%, preferably in the range of from 95% to 99%.

Advantageously, the reaction of the first hydrogenation is carried out in the absence of base.

The reaction medium resulting from the first hydrogenation is subjected to a second hydrogenation, which is carried out in the presence of a heterogeneous catalyst which contains nickel and/or cobalt and/or ruthenium.

The catalyst according to the invention typically contains 1% to 90% of nickel and preferably 5% to 60%, and/or 1% to 90% of cobalt and preferably 5% to 60%, and/or 0.1% to 10% of ruthenium and preferably 1% to 5%. The nickel and/or the cobalt and/or the ruthenium are preferably in the reduced metal form thereof. The catalyst introduced into the reactors according to the invention can nevertheless contain nickel oxides, cobalt oxides or ruthenium oxides, for example in the form of a passivation layer. In addition to nickel or cobalt or ruthenium, the catalyst can contain other metals, such as iron, nickel, chromium, manganese, rhodium, osmium, iridium, platinum or palladium. The catalyst can also be doped with alkali metals such as sodium, potassium, rubidium or cesium, or alkaline-earth metals such as magnesium, calcium, strontium or barium. The catalyst may be in the finely divided state, for example in the form of a Raney catalyst. It may also be in the form of granules, or alternatively may be deposited on a support. Examples of appropriate supports are pumice stone, titanium dioxide, carbon, charcoal, silicon carbide (preferably of beta SiC form), alumina, silica, a mixture of silica and alumina, and steatite.

The catalyst in granular form or deposited on a support may be in any form, such as: sphere, grain, hollow cylinder, three-lobed and four-lobed, and also in the form of cylinders, which have been extruded or compressed, optionally using a pelleting agent.

Advantageously, the second hydrogenation reaction is carried out at a pressure in the range of from 5 to 100 bar, preferably from 20 to 80 bar.

Advantageously, the temperature is in the range of from 50 to 150° C., preferably from 80 to 110° C.

A base is added in order to reduce the selectivity with respect to secondary amine. The base can typically be sodium hydroxide, sodium methoxide, potassium hydroxide, potassium tert-butoxide or ammonia. Ammonia is preferably used. The amount of base used during the second hydrogenation reaction is such that the base/unsaturated nitrile ester or acid nitrile molar ratio at the start of the first hydrogenation is typically in the range of from 0.1 to 4 and preferably in the range of from 0.3 to 2.5.

If the first hydrogenation has taken place in the absence of solvent, the second hydrogenation can also be carried out in the absence of solvent. It can also be carried out in the presence of a solvent. The solvent may be an aromatic hydrocarbon, such as benzene, toluene, xylene or ethylbenzene, or an aliphatic hydrocarbon, such as cyclohexane, pentane, heptane or methylcyclohexane, or an aliphatic fraction, or an alcohol, such as methanol, ethanol, propanol or isopropanol, butanol or an isomer, or an ester such as ethyl acetate or methyl acetate, or an ether such as tetrahydrofuran, diethyl ether, diisopropyl ether, methyl tert-butyl ether or an amide such as dimethylformamide or N-methylpyrrolidone, or a carbonate such as dimethyl carbonate, diethyl carbonate, ethylene carbonate or propylene carbonate; and mixtures thereof.

Preferably, the solvent is chosen from toluene, xylene, cyclohexane or methylcyclohexane, or mixtures thereof.

The concentration of (unsaturated and saturated) nitrile ester or acid nitrile in the solvent can range from 1% to 70% and preferably from 10% to 50% by weight.

The amounts of catalyst to be used in the second hydrogenation can vary according to the activity of the catalyst and the reaction conditions, in particular the temperature and pressure conditions. In successive-charge operations, the weight ratio of catalyst relative to the weight of (saturated and unsaturated) nitrile ester or acid nitrile can range from 0.01 to 1 and preferably from 0.05 to 0.3. The reaction time is in the range of from 1 h to 24 h and preferably in the range from 3 h to 15 h. In continuous operations, the liquid space velocity of the catalyst, expressed in kg/h of nitrile ester divided by kgs of catalyst, can range from 0.01 to 10 $h^{-1}$ and preferably from 0.05 to 2 $h^{-1}$.

Those skilled in the art can thus adjust the reaction conditions of the second hydrogenation, preferably in the abovementioned ranges (amount of catalyst, pressure, temperature) so as to maximize the conversion of the saturated nitrile ester and to obtain a content of saturated nitrile ester in the range of from 0.0001 mol % to 0.5 mol % and preferably from 0.0001 mol % to 0.1 mol % relative to the α,ω-aminoalkanoic ester or acid.

Characteristics Common to Processes A and B

Advantageously, the reaction mixture resulting from the hydrogenation step is subjected to at least one of the following purification steps:
- separation of the catalyst by any solid/liquid separation means known to those skilled in the art,
- separation of the base: in the case of ammonia, by evaporation or aqueous washing, and in the case of the other bases, by aqueous washing or tailing in an apparatus with a short residence time,
- optional separation of the solvent by evaporation or topping,
- separation of the heavy compounds, and in particular of the secondary amine formed during the hydrogenation, by tailing in an apparatus with a short residence time under vacuum at a controlled temperature.

The apparatuses with a short residence time according to the invention are film evaporators, for example falling film evaporators or thin-film evaporators, where the liquid film is created mechanically or by centrifugal force. The typical thin-film evaporator consists of a tubular heat exchange surface equipped with an external heating jacket and fitted, inside a blade rotor, with fixed or mobile scrapers. The function of the blades and scrapers is to spread the liquid in the form of a film of small thickness, in order to promote heat exchange and evaporation of the product, while at the same time limiting its residence time and limiting the formation and the deposits of fouling oligomers and polymers.

The vapors can be condensed in an external or internal condenser. Advantageously, the vapors can be condensed in a condenser inside the evaporator so as to be able to work under an even stronger vacuum of less than 5 or 1 mbar. The term then used is a thin-film short-path evaporator.

Preferentially, the separation of the heavy compounds is carried out in a thin-film evaporator and preferably in a thin-film short-path evaporator.

The heavy-compound separation step is preferably carried out at a temperature of less than 160° C., preferably less than 140° C., preferably less than 130° C.

Those skilled in the art know how to adjust the pressure as a function of the curve of vapor pressure of the saturated α,ω-aminoalkanoic ester or acid, so as to vaporize this acid or ester in the apparatus with a short residence time and to recover, in the distillation residues, the heavy products and in particular the secondary amine formed during the hydrogenation. Because of the low volatility of the saturated α,ω-aminoalkanoic esters of the invention, it is necessary to work under a strong vacuum, generally less than 20 mbar, preferably at a pressure in the range of from 0.5 to 20 mbar, preferably 1 to 20 mbar, and preferably less than 10 mbar, preferably at a pressure of from 0.5 to 5 mbar, preferably from 1 to 5 mbar.

The heavy-compound separation step makes it possible to obtain a composition which comprises a molar ratio between the secondary amine of formula ROOC—$(CH_2)_n$—NH—$(CH_2)_n$—COOR and the α,ω-aminoalkanoic ester or acid in the range of from 0.0001% to 1% and preferably from 0.0001% to 0.5%, and also an initial molar ratio between the ROOC—$(CH_2)_n$—NH—CO—$(CH_2)_n$—$NH_2$ dimer and the α,ω-aminoalkanoic ester or acid in the range of from 0.0001% to 1%.

Use of the Composition

The composition according to the invention can be used as starting material for the production of long-chain polyamide.

In the case of a composition containing α,ω-aminoalkanoic ester, the production of polyamide can in particular be carried out in two steps as described for example in patent document WO 2015/071604, a first step of reaction in the presence of water at a first temperature having the function of at least partially hydrolyzing the ester function, and a second step of reaction at a higher temperature making it possible to obtain the desired degree of polymerization.

The composition according to the invention makes it possible to obtain a polyamide with a degree of polymerization greater than 80, the degree of polymerization of a polyamide being measured by proton NMR, as double the molar ratio between, on the one hand, the amide functions and, on the other hand, the sum of the chain ends (such as amine, acid, alkyl and ester functions).

The composition according to the invention also makes it possible to obtain a polyamide of which the melt rheology increases to a lesser extent at high temperature, as can be measured for example by monitoring the change in the melt viscosity in plate-plate rheometry for 30 minutes at 270° C. The melt viscosity is determined at T0, then after 30 minutes, as is the percentage variation between the two. A lower final viscosity, for example less than 60 000 and preferably less than 45 000 Pa·s, makes it possible to avoid the risks of blocking of the screws of the converting machine in the event of a pause following an unforeseen interruption of production.

Finally, the solution of the present invention has several essential advantages over the prior art:

The composition makes it possible to produce long-chain polyamides with a high degree of polymerization, and which are stable at high temperature.

Compared with the prior art hydrogenation processes, the processes described make it possible to limit in a controlled manner the amount of alkanoic acids or esters relative to the amino acid/ester, thereby making it possible in the end to produce polymers more easily. They also make it possible to obtain the composition according to the invention with a high yield.

EXAMPLES

Example 1: Preparation of a Composition According to the Invention

Unsaturated nitrile ester methyl 10-cyano-9-decenoate (NEI11) is prepared by reacting methyl 9-decenoate with acrylonitrile according to example 5 of WO 2014/122410, followed by evaporation of the toluene and a distillation under reduced pressure so as to obtain NEI11 containing less than 100 molar ppm of methyl decenoate.

13.5 g of Raney cobalt washed with methanol (ActiCat™ 3100 from the company CatAlloy) and 90 g of NEI11 unsaturated nitrile ester and 210 g of toluene are placed in a 1-liter autoclave equipped with a self-suction turbine. The autoclave is flushed with nitrogen, then 4.3 g of ammonia (0.253 mol) are introduced and hydrogen is added so as to bring the pressure to 60 bar. Heating is carried out at 90° C. and the reaction is allowed to take place for 10 hours with vigorous stirring while at the same time maintaining the pressure at 60 bar by addition of hydrogen.

The reactor is then cooled to ambient temperature and the pressure is lowered to atmospheric pressure. The solid is separated from the liquid phase and washed with toluene. The combined liquid phases are evaporated in a rotary evaporator at 30° C. at a pressure which is gradually lowered to 1 mbar. The residual liquid phase is analyzed by gas chromatography: it contains 96% of primary amine, 2.4% of secondary amine, 0.1% of methyl decanoate, 0.1% of saturated nitrile ester methyl 10-cyanodecanoate (NE11) and 1% of toluene (% by weights).

This residual liquid phase is then continuously distilled in a scraped-film short-path evaporator of KDL4 type (UIC). The evaporator is maintained at a pressure of 0.7 mbar. The liquid to be distilled is fed at 150 g/h via the top of the evaporator and forms a film on the exchange surface heated to 120° C. by virtue of roll scrapers. The vapors are condensed on a central exchanger maintained at 15° C.

A composition of methyl 11-aminoundecanoate (AE11) and of methyl decanoate (MD) in a 99.9/0.1 molar ratio is recovered. The weight content of AE11 in the composition is 98.9%, that of saturated nitrile ester methyl 10-cyanodecanoate (NE11) is 0.1%, that of secondary amine of formula $(MeCO_2(CH_2)_{10})_2NH$ is 0.01% and that of toluene is 0.5%. The molar yield of AE11 of the reaction and separation steps is 86%.

Example 2: Polymerization of the Composition Obtained in Example 1

The composition of AE11 and of MD of example 1 (100 g), water (100 g) and 85% phosphoric acid (0.06 g) are introduced into a reactor at total reflux. The reaction mixture is brought to 110° C. for 90 minutes with vigorous stirring. The medium is then lyophilized (so as to remove the water and the methanol), then the lyophilisate is heated to 250° C. under nitrogen flushing in a glass reactor pre-inerted with nitrogen. After 0 h 30 of heating, the polymer obtained is cooled and then analyzed by proton NMR. The degree of polymerization is calculated on the basis of the NMR analysis: it is double the molar ratio between, on the one hand, the amide functions and, on the other hand, the sum of the chain ends (such as amine, acid, alkyl and ester functions).

The melt rheology stability is measured by monitoring the change in the melt viscosity in plate-plate rheometry for 30 minutes at 270° C. The melt viscosity is determined at T0, then after 30 minutes, as is the percentage variation between the two.

The results are reported in table 1.

Comparative Example 3

Example 1 is reproduced with a Raney nickel catalyst (W. R. Grace and Co. Raney® 2800 with a titer of more than 89% Ni). The results are reported in table 1.

The residual liquid phase after evaporation of the toluene contains 95.5% of primary amine, 2.4% of secondary amine, 0.6% of methyl decanoate, 0.1% of saturated nitrile ester NE11 and 1% of toluene (% by weights).

After distillation, a composition of AE11 and of MD in a 99.4/0.6 molar ratio is recovered. The weight content of AE11 in the composition is 98.4%, that of saturated nitrile ester methyl 10-cyanodecanoate (NE11) is 0.1%, that of secondary amine of formula $(MeCO_2(CH_2)_{10})_2NH$ is 0.02% and that of toluene is 0.5%.

Example 4: Polymerization of the Composition Obtained in Example 3

The composition of AE11 and of MD of example 3 is polymerized in the same way as example 2 and the degree of polymerization and the melt rheology stability are measured. The results are reported in table 1.

It is noted that the degree of polymerization is much lower than in example 2.

Comparative Example 5

302 g of commercial 11-aminoundecanoic acid (Sigma-Aldrich) in 1 liter of methanol are introduced into a 2-liter glass reactor equipped with a condenser. 30 normal liters per hour of anhydrous HCl are injected at 60° C. for 3 hours. The reaction mixture is then evaporated in a rotary evaporator under 0.2 bar at 35 and then 45° C. The solid is taken up in 2 liters of ethyl ether and then washed at 5° C. with 380 ml of aqueous 20% sodium hydroxide. After separation by settling out and setting aside of the aqueous phase, the organic phase is washed successively with 200 ml of aqueous 1% sodium hydroxide and then with 4 times 200 ml of demineralized water. The first aqueous phase is re-extracted with 500 ml of ethyl ether and the ethereal phase is washed successively with the aqueous phases previously obtained. The extraction operation is repeated again with 500 ml of ether. The combined organic phases are dried over magnesium sulfate and then evaporated in a rotary evaporator at 20-30° C. while gradually lowering the pressure to 1 mbar.

The liquid phase recovered is continuously distilled in a scraped-film short-path evaporator in the same way as in example 1. A liquid phase more than 99.5% composed of AE11 and containing less than 1 ppm of alkanoic acids or esters is obtained.

Example 6: Polymerization of the Composition Obtained in Example 3

The composition of AE11 containing less than 1 ppm of alkanoic acids or esters, produced in example 5, is polymerized in the same way as in example 2 and the degree of polymerization and the melt rheology stability of the polymer (polyamide 11) are measured.

The results are reported in table 1.

It is noted that the polymer is much less temperature-stable than that of example 2.

Example 7: Preparation of a Composition According to the Invention

Unsaturated nitrile ester methyl 10-cyano-9-decenoate (NEI11) containing less than 100 molar ppm of methyl decenoate is prepared in the same way as in example 1.

Silicone carbide (Sicat CTS-17 with a BET surface area of 24 m$^2$/g and composed of more than 99% of β-sic and less than 0.5% of Fe) is ground and sieved to a particle size of 0.1-0.2 mm, then oven-dried at 120° C. for 2 hours. A 20 g fraction of the powder obtained is subjected to incipient wetness impregnation, to the pore volume, with 11.4 ml of an aqueous solution of ruthenium III nitrosyl nitrate at 0.08 g of Ru ion per ml. The solid is then calcined under an air stream in a tube heated at 2° C./min up to 270° C. and maintained at this temperature for 4 hours.

A part of the solid obtained (10 g) is placed in a fixed-bed reactor. The catalyst is reduced by treatment under hydrogen at 240° C. and then 4.8 normal liters per hour of a mixture of 3% by volume ammonia in hydrogen and 10 ml/h of a solution of methyl 10-cyano-9-decenoate at 30% by weight in toluene are injected. The reactor is maintained at a temperature of 80° C. and an expansion valve ensures a pressure of 50 bar inside the reactor. The liquid phase at the reactor outlet is recovered over a period of 70 hours. After evaporation in a rotary evaporator at 30° C. at a pressure which is gradually reduced to 1 mbar, a residual liquid phase is obtained, which is analyzed by gas chromatography: it contains 95% of primary amine, 3.6% of secondary amine, 0.27% of methyl decanoate, 0.1% of saturated nitrile ester NE11 and 1% of toluene (% by weights).

This residual liquid phase is then distilled in a scraped-film short-path evaporator in the same way as in example 1.

A composition of methyl 11-aminoundecanoate (AE11) and of methyl decanoate (MD) in a 99.73/0.27 molar ratio is recovered. The weight content of AE11 in the composition is 98.9%, that of saturated nitrile ester methyl 10-cyanodecanoate (NE11) is 0.1%, that of secondary amine of formula (MeCO$_2$(CH$_2$)$_{10}$)$_2$NH is 0.02% and that of toluene is 0.5%. The molar yield of AE11 of the reaction and separation steps is 85%.

Example 8: Polymerization of the Composition Obtained in Example 7

The AE11 produced in example 7 is polymerized in the same way as in example 2 and the degree of polymerization and the melt rheology stability are measured.

The result is reported in table 1.

Example 9: Preparation of a Composition According to the Invention

Unsaturated nitrile ester methyl 10-cyano-9-decenoate (NEI11) containing less than 100 molar ppm of methyl decenoate is prepared in the same way as in example 1.

Silicone carbide (Sicat CTS-17 with a BET surface area of 24 m$^2$/g and composed of more than 99% of β-sic and less than 0.5% of Fe) is ground and sieved to a particle size of 0.1-0.2 mm, then oven-dried at 120° C. for 2 hours. A 20 g fraction of the powder obtained is subjected to incipient wetness impregnation, to the pore volume, with 1.14 ml of an aqueous solution of cobalt II nitrate hexahydrate at 0.176 g of Co ion per ml. The solid is then calcined under an air stream in a tube heated at 5° C./min up to 400° C. and maintained at this temperature for 4 hours. It is then reduced under a hydrogen stream at 350° C. for 4 hours, then passivated at ambient temperature under a stream of air depleted to 0.1% oxygen, then to 1% oxygen.

A part of the solid obtained (7 g) is placed in a fixed-bed reactor. The catalyst is reduced by treatment under hydrogen at 240° C. and then 4.8 normal liters per hour of a mixture of 3% by volume ammonia in hydrogen and 10 ml/h of a solution of methyl 10-cyano-9-decenoate at 30% by weight in toluene are injected. The reactor is maintained at a temperature of 80° C. and an expansion valve ensures a pressure of 50 bar inside the reactor. The liquid phase at the reactor outlet is recovered over a period of 70 hours. After evaporation in a rotary evaporator at 30° C. at a pressure which is gradually reduced to 1 mbar, a residual liquid phase is obtained, which is analyzed by gas chromatography: it contains 90% of primary amine, 5% of secondary amine, 0.12% of methyl decanoate, 0.1% of saturated nitrile ester NE11 and 1% of toluene (% by weights).

This residual liquid phase is then distilled in a scraped-film short-path evaporator in the same way as in example 1.

A composition of methyl 11-aminoundecanoate (AE11) and of methyl decanoate (MD) in a 99.88/0.12 molar ratio is recovered.

Example 10: Polymerization of the Composition Obtained in Example 9

The AE11 produced in example 9 is polymerized in the same way as in example 2 and the degree of polymerization and the melt rheology stability are measured.

The results are reported in table 1.

Example 11: Preparation of a Composition According to the Invention

Unsaturated nitrile ester methyl 10-cyano-9-decenoate (NEI11) containing less than 100 molar ppm of methyl decenoate is prepared in the same way as in example 1.

10 g of palladium at 2% on reduced carbon powder (BASF Italy reference 51678063-5254) and 90 g of unsaturated nitrile ester NEI11 and 210 g of toluene are introduced into a 1-liter autoclave equipped with a self-suction turbine. The autoclave is flushed with nitrogen, then hydrogen is added so as to maintain a pressure of 5 bar. After eight hours with vigorous stirring at 30-40° C., the reaction medium is expanded and then filtered. Gas chromatography analysis shows that the NEI11 has been 97% converted.

The liquid phase is again introduced into the autoclave containing 13.5 g of Raney nickel washed with methanol (W. R. Grace and Co. Raney® 2800 with a titer of more than 89% Ni). The autoclave is flushed with nitrogen, then 4.3 g of ammonia (0.253 mol) are introduced and hydrogen is added so as to bring the pressure to 60 bar. Heating is carried out at 90° C. and the reaction is allowed to take place for 12 hours with vigorous stirring while at the same time maintaining the pressure at 60 bar by addition of hydrogen.

The reactor is then cooled to ambient temperature and the pressure is lowered to atmospheric pressure. The solid is separated from the liquid phase and washed with toluene. The combined liquid phases are evaporated in a rotary evaporator at 30° C. at a pressure which is gradually lowered to 1 mbar. The residual liquid phase is analyzed by gas chromatography: it contains 96% of primary amine, 2.3% of secondary amine, 0.03% of methyl decanoate, 0.03% of saturated nitrile ester NE11 and 1% of toluene (% by weights).

This residual liquid phase is then distilled in a scraped-film short-path evaporator in the same way as in example 1.

A composition of methyl 11-aminoundecanoate (AE11) and of methyl decanoate (MD) in a 99.97/0.03 molar ratio is recovered.

Example 12: Polymerization of the Composition Obtained in Example 11

The AE11 produced in example 11 is polymerized in the same way as in example 2 and the degree of polymerization and the melt rheology stability are measured.

The results are reported in table 1.

Example 13

A solution containing 2% by weight of heptanoic acid in methanol (5 grams) is sprayed onto 99.9 g of commercial powdered 11-aminoundecanoic acid (Sigma-Aldrich) with vigorous stirring. The methanol is then evaporated off under reduced pressure. A mixture of 11-aminoundecanoic acid containing 0.15 mol % of heptanoic acid is obtained.

Example 14: Polymerization of the Composition Obtained in Example 13

The composition of 11-aminoundecanoic acid and heptanoic acid of example 13 (100 g), to which 85% phosphoric acid (0.06 g) has been added, is introduced into a glass reactor pre-inerted with nitrogen. The reaction mixture is brought to 250° C., under nitrogen flushing, with vigorous stirring. After 0 h 30 of heating, the polymer obtained is cooled.

The degree of polymerization and the melt rheology stability are measured in the same way as in example 2.

The results are reported in table 1.

TABLE 1

| Example | Molar ratio Alkanoic acid/ester to Aminoalkanoic acid/ester | Degree of polymerization | Melt viscosity at 270° C. (Pa · s) | | |
|---|---|---|---|---|---|
| | | | Initial | After 30 minutes | Variation over the course of 30 minutes |
| Example 2 | 0.1% | 140 | 16 800 | 44 300 | +164% |
| Comparative example 4 | 0.6% | 70 | 620 | 1120 | +80% |
| Comparative example 6 | <1 ppm | 150 | 21 200 | 75 200 | +254% |
| Example 8 | 0.27% | 120 | 4090 | 10 200 | +149% |
| Example 10 | 0.12% | 135 | 15 900 | 41 300 | +160% |
| Example 12 | 0.03% | 145 | 19 100 | 55 700 | +192% |
| Example 14 | 0.15% | 145 | 17 200 | 45 800 | +166% |

The invention claimed is:

1. A composition comprising at least one α,ω-aminoalkanoic acid or ester and at least one alkanoic acid or ester, wherein:
   the α,ω-aminoalkanoic ester or acid has the formula $H_2N-(CH_2)_n-COOR$ with n=9 to 13 and R is an alkyl group or a hydrogen,
   the alkanoic acid or ester has the formula $R_1-COOR_2$ with $R_1$ being a linear or branched alkyl group of formula $C_mH_{2m+1}$ or $C_mH_{2m-1}$ or $C_mH_{2m-3}$ where m=6 to 20 and $R_2$ is an alkyl group or a hydrogen,
   the molar ratio between alkanoic acid(s) or ester(s) and α,ω-aminoalkanoic ester(s) or acid(s) is in the range of from 0.001% to 0.4%.

2. The composition as claimed in claim 1, wherein n=10 or 11, and R is a methyl or ethyl or butyl group or a hydrogen.

3. The composition as claimed in claim 1, wherein $R_1$ is a linear alkyl group of composition $C_{n-1}H_{2n-1}$ and $R_2$ is a methyl or ethyl group or a hydrogen.

4. The composition as claimed in claim 1, wherein the molar ratio between alkanoic acid(s) or ester(s) and α,ω-aminoalkanoic ester(s) or acid(s) is in the range of from 0.01% to 0.2%.

5. The composition as claimed in claim 1, wherein it also comprises an acid nitrile or a nitrile ester of formula $NC-(CH_2)_{(n-1)}-COOR$, in which the molar ratio of nitrile relative to the α,ω-aminoalkanoic ester or acid is in the range of from 0.0001% to 0.5%.

6. The composition as claimed in claim 1, wherein it also comprises a secondary amine of formula $ROOC-(CH_2)_n-NH-(CH_2)_n-COOR$, in which the molar ratio relative to the α,ω-aminoalkanoic ester or acid is in the range of from 0.0001% to 1%.

7. The composition as claimed in claim 1, wherein it also comprises $ROOC-(CH_2)_n-NH-CO-(CH_2)_n-NH_2$ dimer, the molar ratio of dimer relative to the α,ω-aminoalkanoic ester or acid being in the range of from 0.0001% to 5%.

8. The composition as claimed in claim 1, wherein it also comprises at least one compound chosen from: compounds that are inert with respect to the polymerization, alcohols, water, and mixtures thereof.

9. The composition as claimed in claim 8, wherein the compounds that are inert with respect to the polymerization are chosen from: aromatic hydrocarbons; aliphatic hydrocarbons; an aliphatic fraction; an ether; and mixtures thereof.

10. The composition as claimed in claim 8, wherein the alcohols are chosen from methanol, ethanol, butanol, and mixtures thereof.

11. The composition as claimed in claim 8, wherein the content of inert compounds, of alcohol and/or of water is less than 90%, by weight relative to the total weight of the composition.

12. The composition as claimed in claim 1, wherein the content of α,ω-aminoalkanoic ester or acid is greater than 10%, by weight relative to the total weight of the composition.

13. A polymer, in particular polyamide, obtained by polymerization of the composition of claim 1, wherein the degree of polymerization thereof is greater than 80.

* * * * *